US006841517B1

(12) United States Patent
Feucht et al.

(10) Patent No.: US 6,841,517 B1
(45) Date of Patent: Jan. 11, 2005

(54) SELECTIVE HERBICIDES ON BASIS OF N-ARYL-TRIAZOLINE(THI)ONES

(75) Inventors: Dieter Feucht, Monheim (DE); Mark Wilhelm Drewes, Langenfeld (DE); Peter Dahmen, Neuss (DE); Birgit Krauskopf, Leawood, KS (US); Mathias Kremer, Burscheid (DE); Rolf Pontzen, Leichlingen (DE); Arndt Wellmann, Odenthal (DE); Wilhelm Haas, Pulheim (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/089,294

(22) PCT Filed: Sep. 18, 2000

(86) PCT No.: PCT/EP00/09089

§ 371 (c)(1),
(2), (4) Date: Mar. 27, 2002

(87) PCT Pub. No.: WO01/22819

PCT Pub. Date: Apr. 5, 2001

(30) Foreign Application Priority Data

Sep. 30, 1999 (DE) .......................................... 199 46 855
Dec. 22, 1999 (DE) .......................................... 199 62 017

(51) Int. Cl.[7] ........................ A01N 43/653; A01N 25/32
(52) U.S. Cl. .................. 504/132; 504/134; 504/136; 504/139; 504/212; 504/213; 504/214; 504/215; 504/241; 504/246; 504/273
(58) Field of Search .......................... 504/132, 134, 504/136, 139, 212, 213, 214, 215, 241, 246, 273

(56) References Cited

U.S. PATENT DOCUMENTS

| 4,318,731 | A | 3/1982 | Kajioka et al. ................ 71/92 |
|---|---|---|---|
| 4,639,266 | A | 1/1987 | Heubach et al. ............... 71/92 |
| 4,702,763 | A | 10/1987 | Maravetz ....................... 71/90 |
| 4,743,291 | A | 5/1988 | Maravetz ....................... 71/92 |
| 4,806,145 | A | 2/1989 | Maravetz ....................... 71/92 |
| 4,818,275 | A | 4/1989 | Theodoridis ................... 71/92 |
| 4,818,276 | A | 4/1989 | Maravetz et al. .............. 71/92 |
| 4,845,232 | A | 7/1989 | Matsui et al. ................ 548/265 |
| 4,881,966 | A | 11/1989 | Nyffeler et al. ................ 71/92 |
| 4,906,284 | A | 3/1990 | Theodoridis ................... 71/92 |
| 4,909,831 | A | 3/1990 | Keifer et al. .................. 71/92 |
| 4,909,833 | A | 3/1990 | Kajioka et al. ................ 71/92 |
| 4,919,708 | A | 4/1990 | Maravetz ....................... 71/92 |
| 5,006,148 | A | 4/1991 | Fischer et al. ................. 71/92 |
| 5,035,740 | A | 7/1991 | Poss .............................. 71/93 |
| 5,041,155 | A | 8/1991 | Theodoridis ................... 71/92 |
| 5,125,958 | A | 6/1992 | Poss .............................. 71/92 |
| 5,174,809 | A | 12/1992 | Theodoridis ................... 71/92 |
| 5,208,212 | A | 5/1993 | Poss et al. .................... 504/139 |
| 5,214,154 | A | 5/1993 | Theodoridis ............. 548/263.2 |
| 5,217,520 | A | 6/1993 | Poss ............................ 504/128 |
| 5,294,595 | A | 3/1994 | Theodoridis ................ 504/139 |
| 5,464,810 | A | 11/1995 | Haas et al. ................... 504/273 |
| 5,476,946 | A | 12/1995 | Linker et al. ................ 504/273 |
| 5,494,886 | A | 2/1996 | Kehne et al. ................. 504/215 |
| 5,529,976 | A | 6/1996 | Kehne et al. ................. 504/213 |
| 5,554,580 | A | 9/1996 | Fischer et al. .............. 504/281 |
| 5,576,440 | A | 11/1996 | Kehne et al. ................. 546/294 |
| 5,648,315 | A | 7/1997 | Lorenz et al. ............... 504/214 |
| 5,663,362 | A | 9/1997 | Haas et al. ................. 548/263.2 |
| 5,811,373 | A | 9/1998 | Santel et al. ................. 504/139 |
| 5,885,934 | A | * 3/1999 | Heistracher et al. ......... 504/169 |
| 5,925,597 | A | 7/1999 | Lorenz et al. ............... 504/212 |
| 6,077,813 | A | 6/2000 | Linker et al. ................. 504/272 |
| 6,211,118 | B1 | * 4/2001 | Hoshi ........................... 504/134 |
| 6,239,306 | B1 | 5/2001 | Lorenz et al. ............... 558/257 |
| 6,297,192 | B1 | 10/2001 | Dollinger et al. ............ 504/139 |
| 6,331,507 | B1 | 12/2001 | Linker et al. ............... 504/244 |
| 6,420,316 | B1 | 7/2002 | Linker et al. ............... 504/273 |

FOREIGN PATENT DOCUMENTS

| CA | 1242730 | 10/1988 |
|---|---|---|
| CA | 2102750 | 5/1994 |
| DE | 196 10 786 | 9/1997 |
| DE | 196 35 060 | 3/1998 |
| DE | 196 35 074 | 3/1998 |
| DE | 198 02 697 | 7/1999 |
| EP | 0 112 799 | 7/1984 |
| EP | 0 609 734 | 8/1994 |
| EP | 0 931 456 | 7/1999 |
| WO | 88/09617 | 12/1988 |
| WO | 94/09629 | 5/1994 |
| WO | 96/03878 | 2/1996 |
| WO | 98/12923 | 4/1998 |
| WO | 99/51099 | 10/1999 |
| WO | 00/08934 | 2/2000 |

OTHER PUBLICATIONS

Weeds, 15, (month unavailable) 1967, pp. 20–22, Calculating Synergistic and Antagonistic Responses of Herbicide Combinations by S. R. Colby.
Registry No.: 157739–46–3 no date.
United States Statutory Invention Registration, Reg. No. H1711, Published: Feb. 3, 1998, Herbicidal Mixtures, Smith III.
Database Cropu Online! Derwent Publication Ltd. ; 1997, Owen M D K et al: "Evaluation on BAY FOE 5043, sulfentrazone, and AC 299, 263 for weed control in soybeans, Crawfordsville, Iowa, 1996." retrieved from STN Database accession No. 1997–88900 XP002159116, Zusammenfassung & Res. Rep North Cent. Weed Sci. Soc. (53, 389, 1996) 1 Tab.
British Crop Protection Council: "The Pesticide Manual, Tenth Edition" Pesticide Manual, GB, Famham, BCPC, vol. Ed. 10, pp. 1335–1341 XP002031460 ISBN: 0–948404–79–5 der Index, soweit er sich auf Herbizide bezieht.
Registry No.: 173980–17–1.
Registry No.: 157739–55–4.
Registry No.: 157739–37–2.

* cited by examiner

*Primary Examiner*—S. Mark Clardy
(74) *Attorney, Agent, or Firm*—Richard E. L. Henderson; Raymond J. Harmuth

(57) ABSTRACT

The invention relates to novel herbicidal synergistic active compound combinations comprising on the one hand known N-aryl-triazolin(ethi)ones and on the other hand known herbicidally active compounds and/or compounds which improve crop plant compatibility and which can be used with particularly good results for the selective control of weeds in various crops of useful plants.

7 Claims, No Drawings

SELECTIVE HERBICIDES ON BASIS OF N-ARYL-TRIAZOLINE(THI)ONES

This application has been filed under 35 USC as the national stage of international application PCT/EP00/09089, filed Sep. 18, 2000.

The invention relates to novel herbicidal synergistic active compound combinations comprising on the one hand known N-aryl-triazolin(ethi)ones and on the other hand known herbicidally active compounds and/or compounds which improve crop plant compatibility and which can be used with particularly good results for the selective control of weeds in various crops of useful plants.

N-aryl-triazolin(ethi)ones form, as herbicidally active substances, part of the subject-matter of a number of patent applications (cf. DE-A-3024316, DE-A-3514057, DE-A-3636318, EP-A-220952, EP-A-370332, EP-A-597360, EP-A-609734, U.S. Pat. No. 4,702,763, 4,806,145, 4,818,275, 4,906,284, 4,909,831, 5,035,740, 5,041,155, WO-A-85/01637, WO-A-85/04307, WO-A-86/02642, WO-A-86/04481, WO-A-87/00730, WO-A-87/03782, WO-A-88/09617, WO-A-90/02120, WO-A-95/30661, WO-A-99/37153). However, the known N-aryl-triazolin(ethi)ones have a number of gaps in their activity.

Surprisingly, it has now been found that a number of known active compounds from the group of the N-aryl-triazolin(ethi)ones exhibit, when used together with known herbicidally active compounds, synergistic effects with respect to their herbicidal action, and can be used particularly advantageously as broad-spectrum combination preparations for the selective control of weeds in crops of useful plants, such as, for example, in cotton, barley, potatoes, maize, rice, soya, sunflowers, wheat and sugar cane.

The invention provides selective herbicidal compositions, characterised in that they contain an effective amount of an active compound combination comprising (a) at least one N-aryl-triazolin(ethi)one of the general formula (I)

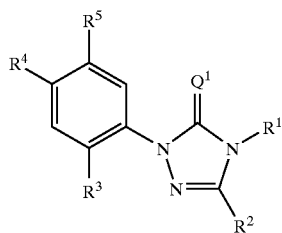

(I)

in which $Q^1$ represents oxygen or sulphur, $R^1$ represents optionally halogen-substituted alkyl having 1 to 5 carbon atoms, $R^2$ represents optionally halogen-substituted alkyl having 1 to 5 carbon atoms, $R^3$ represents hydrogen or halogen, $R^4$ represents cyano, thiocarbamoyl or halogen, and $R^5$ represents nitro, cyano, carboxyl, carbamoyl, thiocarbamoyl, hydroxyl, mercapto, amino, hydroxyamino, aminosulphonyl, halogen, represents in each case optionally cyano-, hydroxyl-, $C_1$–$C_4$-alkoxy-, $C_1$–C4-alkylcarbonyl- and/or $C_1$–$C_4$-alkoxycarbonyl-substituted alkyl, alkoxy, alkylthio, alkylsulphinyl, alkylsulphonyl, alkylcarbonyl, alkoxycarbonyl or alkylamino having in each case 1 to 6 carbon atoms, represents in each case optionally cyano-, carboxyl-, halogen- and/or $C_1$–$C_4$-alkoxycarbonyl-substituted alkenyl, alkinyl, alkenyloxy or alkinyloxy having in each case 2 to 6 carbon atoms, represents in each case optionally halogen-substituted alkylcarbonylamino, alkoxycarbonylamino, alkylsulphonylunino, N,N-bis-alkylsulphonyl-amino or N-alkylcarbonyl-N-alkylsulphonyl-amino having in each case 1 to 6 carbon atoms in the alkyl groups, or represents in each case optionally cyano-, halogen-, $C_1$–$C_4$-alkyl-, $C_1$–C4-halogenoalkyl-, $C_1$–$C_4$-alkoxy- or $C_1$–$C_4$-halogenoalkoxy-substituted N-phenylcarbonyl-N-alkylsulphonyl-amino, N-pyridylcarbonyl-N-alkylsulphonyl-amino, N-furylcarbonyl-N-alkylsulphonyl-amino or N-thienylcarbonyl-N-alkylsulphonyl-amino having in each case 1 to 6 carbon atoms in the alkyl groups, ("Active Compounds of Group 1")

and (b) at least one compound from a second group of herbicides comprising the active compounds listed below:

2-chloro-N-(ethoxymethyl)-N-(2-ethyl-6-methyl-phenyl)-acetamide (acetochlor), 5-(2-chloro-4-trifluoromethyl-phenoxy)-2-nitro-benzoic acid sodium salt (acifluorfen-sodium), 2-chloro-6-nitro-3-phenoxy-benzenamine (aclonifen), 2-chloro-N-(methoxymethyl)-N-(2,6-diethyl-phenyl)-acetamide (alachlor), N-ethyl-N'-1-propyl-6-methylthio-1,3,5-triazine-2,4-diamine (ametryn), 4-amino-N-(1,1-dimethyl-ethyl)-4,5-dihydro-3-(1-methyl-ethyl)-5-oxo-1H-1,2,4-triazole-1-carboxamide (amicarbazone), N-(4,6-dimethoxy-pyrimidin-2-yl)-N'-(N-methyl-N-methyl-sulphonyl-sulphamoyl)-urea (amidosulfiurn), 1H-1,2,4-triazol-3-amine (amitrole), 6-chloro-4-ethylamino-2-isopropylamino-1,3,5-triazine (atrazine), N-(4,6-dimethoxy-pyrimidin-2-yl)-N'-[1-methyl-4-(2-methyl-2H-tetrazol-5-yl)-1H-pyrazol-5-yl-sulphonyl]-urea (azimsulfuron), 2-[2,4dichloro-5-(2-propinyloxy)-phenyl]-5,6,7,8-tetrahydro-1,2,4-triazolo-[4,3-a]-pyridin-3(2H)-one (azafenidin), N-benzyl-2-(4-fluoro-3-trifluoromethyl-phenoxy)-butanamide (beflubutamide), 4-chloro-2-oxo-3(2H)-benzothiazoleacetic acid (benazolin), N-butyl-N-ethyl-2,6-dinitro-4-tri-fluoromethyl-benzenamine (benfluralin), N-(4,6-dimethoxy-pyrimidin-2-yl)-N'-(2-methoxycarbonyl-phenylmethylsulphonyl)-urea (bensulfuron), methyl 2-[2-[4-(3,6-dihydro-3-methyl-2,6-dioxo-4-trifluoromethyl-1(2H)-pyrimidinyl)phenoxy]methyl]-5-ethyl-phenoxy-propanoate (benzfendizone), 3-(2-chloro-4-methylsulphonyl-benzo-yl)4-phenylthio-bicyclo-[3.2.1]-oct-3-en-2-one (benzobicyclon), ethyl N-benzoyl-N-(3,4-dichlorophenyl)-DL-alaninate (benzoylprop-ethyl), 3-i-propyl-1H-2,1,3-benzo-thiadiazin-4(3H)-one (bentazone), methyl 5-(2,4-dichloro-phenoxy)-2-nitro-benzoate (bifenox), 2,6-bis-(4,6-dimethoxy-pyrimidin-2-yl-oxy)-benzoic acid sodium salt (bis-pyribac-sodium), 2-bromo-3,3-dimethyl-N-(1-methyl-1-phenyl-ethyl)-butanamide (bromobutide), O-(2,4-dinitro-phenyl) 3,5-dibromo-4-hydroxy-benzaldehyde-oxime (bromofenoxim), 3,5-dibromo-4-hydroxy-benzonitrile (bromoxynil), N-butoxy-methyl-2-chloro-N-(2,6-diethyl-phenyl)-acetamide (butachlor), [1,1-dimethyl-2-oxo-2-(2-propenyloxy)]-ethyl 2-chloro5-(3,6-dihydro-3-methyl-2,6-dioxo-4-trifluoromethyl-1(2H)pyrimidinyl)-benzoate (butafenacil-allyl), 2-(1-ethoximino-propyl)-3-hydroxy-5-[2,4,6-trimethyl-3-(1-oxo-butyl)-phenyl]-2-cyclohexen-1-one (butroxydim), S-ethyl bis-(2-methyl-propyl)-thiocarbamiate (butylate), N,N-diethyl-3-(2,4,6-trimethylphenylsulphonyl)-1H-1,2,4-triazole-1-carboxamide (cafenstrole), 2-[1-[(3-chloro-2-propenyl)-oxy-imino]-propyl]-3-hydroxy-5-(tetrahydro-2H-pyran-4-yl)-2-cyclohexen-1-one (caloxydim, tepraloxydim), 2-(4-chloro-2-fluoro-5-(2-chloro-2-ethoxycarbonyl-ethyl)-phenyl)-4-difluoromethyl-5-methyl-2,4-dihydro-3H-1,2,4-triazol-3-one (carfentrazone-ethyl), 2,4-dichloro-1-(3-methoxy-4-nitro-phenoxy)-benzene (chlomethoxyfen), 3-amino-2,5-dichloro-benzoic acid (chloramben), N-(4-chloro-6-methoxy-pyrimidin-2-yl)-N'-(2-ethoxycarbonyl-phenylsulphonyl)-urea (chlorimuron-ethyl), 1,3,5-trichloro-2-(4-nitro-phenoxy)benzene (chlomitrofen), N-(4-methoxy-6-methyl- 1,3,5-triazin-2-yl)-N'-(2-chloro-phenylsulphonyl)-urea (chlorsulfuron), N'-(3-chloro-4-methyl-phenyl)-N,N-dimethyl-urea (chlortoluron), ethyl 2-chloro-3-[2-chloro-5-(1,3,4,5,6,7-hexahydro-1,3-dioxo-2H-isoindol-2-yl)-phenyl]-2-propanoate (cinidon-ethyl), N-(4,6-dimethoxy-1,3,5-triazin-2-yl)-N'-(2-(2-methoxy-ethoxy)-phenylsulphonyl)-urea (cinosulfuiron), 2-[1-[2-(4-chloro-phenoxy)-propoxyamino]butyl]-5-(tetrahydro-2H-thiopyran-3-yl)-1,3-cyclohexanedione (clef-oxydim), (E,E)-(+)-2-[1 -[[(3-chloro-2-propenyl)-oxy]-imino]-propyl]-5-[2-(ethylthio)-propyl]-3-hydroxy-2-cyclohexen-1-one (clethodim), prop-2-inyl (R)-2-[4-(5-chloro-3-fluoro-pyridin-2-yl-oxy)-phenoxy]-propanoate (clodinafop-propargyl), 3,6-dichloro-pyridine-2-carboxylic acid (clopyralid), methyl 3-chloro-2-[(5-ethoxy-7-fluoro[1,2,4]triazolo[1,5-c]pyrimidin-2-yl-sulphonyl)-amino]-benzoate (cloransulam-methyl), 2-chloro-4-ethylamino-6-(1-cyano-1-methyl-ethylamino)-1,3,5-triazine (cyanazine), N-(4,6-dimethoxy-pyrimidin-2-yl)-N'-(2-cyclopropylcarbonyl-phenyl-sulphonyl)-urea (cyclosulfamuron), 2-(1-ethoximinobutyl)-3-hydroxy-5-(tetrahydro-2H-thiopyran-3-yl)-2-cyclohexen-1-one (cycloxydim), butyl (R)-2-[4-(4-cyano-2-fluoro-phenoxy)-phenoxy]-propanoate (cyhalofop-butyl), 2,4-dichloro-phenoxyacetic acid (2,4-D), 3,6-dichloro-2-methoxy-benzoic acid (dicamba), (R)-2-(2,4-dichloro-phenoxy)-propanoic acid (dichlorprop-P), methyl-2-[4-(2,4-dichloro-phenoxy)-phen-oxy]-propanoate (diclofop-methyl), N-(2,6-dichloro-phenyl)-5-ethoxy-7-fluoro-[1,2,4]-triazolo-[1,5-c]-pyrimidine-2-sulphonamide (diclosulam), 1,2-dimethyl-3,5-diphenyl-1H-pyrazolium methylsulphate (difenzoquat), N-(2,4-difluoro-phenyl)-2-(3-trifluoromethyl-phenoxy)-pyridine-3-carboxamide (diflufenican), 2-[1-[(3,5-difluoro-phenyl)-amino-carbonyl-hydrazono]-ethyl]-pyridine-3-carboxylic acid (diflufenzo-pyr), S-(1-methyl-1-phenyl-ethyl) 1-piperidine-carbothioate (dimepiperate), 2-chloro-N-(2,4-dimethyl-3-thienyl)-N-(2-methoxy-1-methyl-ethyl)-acetamide (dimethenamid), 2-amino-4-(1-fluoro-1-methyl-ethyl-6-(1-methyl-2-(3,5-dimethyl-phenoxy) ethylamino)-1,3,5-triazine (dimexyflam), N3,N3-diethyl-2,4-dinitro-6-trifluoromethyl-1,3-diamino-benzene (dinitramine), 6,7-dihydro-dipyrido[1,2-a:2',1'-c]pyrazindiium (diquat), S,S-dimethyl 2-difluoromethyl-4-i-butyl-6-trifluoromethyl-pyridine-3,5-dicarbothioate (dithiopyr), N'-(3,4-dichloro-phenyl)-N,N-dimethyl-urea (diuron), 2-[2-(3-chloro-phenyl)-oxiranylmethyl]-2-ethyl-1H-indene-1,3(2H)-dione (epropodan), S-ethyl dipropylthiocarbamate (EPTC), S-(phenylmethyl) N-ethyl-N-(1,2-dimethyl-propyl)-thiocarbamate (esprocarb), N-ethyl-N-(2-methyl-2-propenyl)-2,6-dinitro-4-trifluoromethyl-benzenamine (ethalfluralin), 2-ethoxy-1-methyl-2-oxo-ethyl (S)-2-chloro-5-(2chloro-4-trifluoromethyl-phenoxy)-benzoate (ethoxyfen), N-(4,6-dimethoxy-pyrimidin-2-yl)-N'-(2-ethoxy-phenoxysulphonyl)-urea (ethoxysulfuron), ethyl (R)-2-[4-(6-chloro-benzoxazol-2-yl-oxy)-phenoxy]-propanoate (fenoxaprop-(P)-ethyl), 4-(2-chloro-phenyl)-N-cyclohexyl-N-ethyl-4,5-dihydro-5-oxo-1H-tetrazole-1-carboxamide (fentrazamid), isopropyl N-benzoyl-N-(3-chloro-4-fluoro-phenyl)-DL-alaninate (flamprop-isopropyl), isopropyl N-benzoyl-N-(3-chloro-4-fluoro-phenyl)-L-alaninate (flamprop-isopropyl-L), methyl N-benzoyl-N-(3-chloro-4-fluoro-phenoxy)-DL-alaninate (flamprop-methyl), N-(2,6-difluoro-phenyl)-8-fluoro-5-methoxy-[1,2,4]-triazolo-[1,5-c]-pyrimidine-2-sulphonamide (florasulam), butyl (R)-2-[4-(5-trifluoromethyl-pyridin-2-yl-oxy)-phenoxy]-propanoate (fluazifop, -butyl, -P-butyl), i-propyl 5-(4-bromo-1-methyl-5-trifluoromethyl-1H-pyrazol-3-yl)-2-chloro-4-fluoro-benzoate (fluazolate), N-(4-fluoro-phenyl)-N-i-propyl-2-(5-trifluoromethyl-1,3,4-thiadiazol-2-yl-oxy)-acetamide (flufenacet), N-(2,6-difluoro-phenyl)-5-methyl-1,2,4-triazolo[1,5-a]-pyrimidine-2-sulphonamide (flumetsulam), pentyl [2-chloro-4-fluoro-5-(1,3,4,5,6,7-hexahydro-1,3-dioxo-2H-isoindol-2-yl)-phenoxy]-acetate (flumiclorac-pentyl), 2-[7-fluoro-3,4-dihydro-3-oxo-4-(2-propinyl)-2H-1,4-benzoxazin-6-yl]-4,5,6,7-tetrahydro-1H-isoindole-1,3-dione (flumioxazin), 2-[4-chloro-2-fluoro-5-[(1-methyl-2-propinyl)-oxy]-phenyl]4,5,6,7-tetrahydro-1H-iso-indole-1,3(2H)-dione (flumipropyn), ethoxycarbonylmethyl 5-(2-chloro-4-trifluoromethyl-phenoxy)-2-nitro-benzoate (fluoroglycofen-ethyl), 1-(4-chloro-3-(2,2,3,3,3-pentafluoro-propoxymethyl)-phenyl)-5-phenyl-1H-1,2,4-triazole-3-carboxamide (flupoxam), 1-isopropyl-2-chloro-5-(3,6-dihydro-3-methyl-2,6-dioxo-4-trifluoromrethyl-1(2H)-pyrimidyl)-benzoate (flupropacil), N-(4,6-dimethoxy-pyrimidin-2-yl)-N'-(3-methoxycarbonyl-6-trifluoromethyl-pyridin-2-yl-sulphonyl)-urea sodium salt (flupyrsulfuron-methyl-sodium), 9-hydroxy-9H-flueorene-9-carboxylic acid (flurenol), (4-amino-3,5-dichloro-6-fluoro-pyridin-2-yl-oxy)-acetic acid (2-butoxy-1-methyl-ethyl ester, 1-methyl-heptyl ester) (fluroxypyr, -butoxypropyl, -meptyl), 5-methylamino-2-phenyl-4-(3-trifluoromethyl-phenyl)-3(2H)-furanone (flurtamone), methyl [(2-chloro-4-fluoro-5-(tetrahydro-3-oxo-1H,3H-[1,3,4]-thiadiazolo-[3,4-a]-pyridazin-1-yliden)-amino)-phenyl]-thio-acetate (fluthiacet-methyl), 5-(2-chloro-4-trifluoromethyl-phenoxy)-N-methylsulphonyl-2-nitro-benzamide (fomesafen), 2-amino-4-(hydroxymethylphosphinyl)-butanoic acid (ammonium salt) (glufosinate-(ammonium)), N-phosphonomethyl-glycine (isopropylammonium) (glyphosate, isopropylammonium), N-(4,6-dimethoxy-pyrimidin-2-yl)-N'-(3-chloro-4-methoxy-carbonyl-1-methyl-pyrazol-5-yl-sulphonyl)-urea (halosulfuron-methyl), (R)-2-[4-(3-chloro-5-trifluoromethyl-pyridin-2-yl-oxy)-phenoxy]-propanoic acid (methyl ester, 2-ethoxy-ethyl ester, butyl ester) (haloxyfop, -methyl, -P-methyl, -ethoxyethyl, -butyl), 3-cyclohexyl-6-dimethylamino-1-methyl-1,3,5-triazine-2,4(1H,3H)-dione (hexazinone), methyl 2-(4,5-dihydro-4-methyl-4-isopropyl-5-oxo-1H-imidazol-2-yl)-4-methyl-beeeoate (imazamethabenz-methyl), 2-(4,5-dihydro-4-methyl-4-isopropyl-5-oxo-1H-imidazol-2-yl)-5-methyl-pyridine-3-carboxylic acid (imazamethapyr), 2-(4,5-dihydro-4-methyl-4-i-propyl-5-oxo-1H-imidazol-2-yl)-3-pyridine-carboxylic acid (imazapyr), 2-(4,5-dihydro-4-methyl-4-isopropyl-5-oxo-1H-imidazol-2-yl)-5-methoxymethyl-pyridine-3-carboxylic acid (imazamox), 2-(4,5-dihydro-4-methyl-4-isopropyl-5-oxo-1H-imidazol-2-yl)-quinoline-3-carboxylic acid (imazaquin), 2-(4,5-dihydro-4-methyl-4-i-propyl-5-oxo-1H-imidazol-2-yl)-5-ethyl-pyridine-3-carboxylic acid (imazethapyr), N-(4,6-dimethoxy-pyrimidin-2-yl)-N'-(2-chloro-imidazo[1,2-a]-pyridin-3-yl-sulphonyl)-urea (imazosulfuron), N-(4-methoxy-6-methyl-1,3,5-triazin-2- yl)-N'-(5-iodo-2-methoxycarbonyl-phenylsulphonyl)-urea sodium salt (iodo-sulfuron-methyl-sodium), 4-hydroxy-3,5-diiodo-benzonitrile (ioxynil), N,N-dimethyl-N'-(4-isopropyl-phenyl)-urea (isoproturon), N-(3-(1-ethyl-1-methyl-propyl)isoxazol-5-yl)-2,6-dimethoxy-benzamide (isoxaben), (4-chloro-2-methylsulphonylphenyl)-(5-cyclopropyl-isoxazo]4-yl)-methanone (isoxachlortole), (5-cyclopropylisoxazol-4-yl)-(2-methylsulphonyl-4-trifluoromethyl-phenyl)-methanone (isoxaflutole), 2-[2-[4-[(3,5-dichloro-2-pyridinyl)-oxy]-phenoxy]-1-oxo-propyl]-isoxazolidine (isoxapyrifop), (2-ethoxy-1-methyl-2-oxo-ethyl)-5-(2-chloro-4-trifluoromethyl-phenoxy)-2-nitro-benzoate (lactofen), N'-(3,4-dichloro-phenyl)-N-methoxy-N-methyl-urea (linuron), (4-chloro-2-methyl-phenoxy)-acetic acid (MCPA), 2-(4-chloro-2-methyl-phenoxy)-propionic acid (mecoprop), 2-(2-benzothiazolyloxy)-N-methyl-N-phenyl-acetamide (mefenacet), 2-(4-methylsulphonyl-2-nitro-benzoyl) 1,3-cyclohexanedione (mesotrione), 4-amino-3-methyl-6-phenyl-1,2,4triazin-5 (4H)-one (metamitron), 2-chloro-N-(2,6-dimethyl-phenyl)-N-(1H-pyrazol-1-yl-methyl)-acetamide (metazachlor), N'-(4-(3,4-dihydro-2-methoxy-2,4,4-trimethyl-2H-1-benzopyran-7-yl-oxy)phenyl)-N-methoxy-N-methyl-urea (metobenzuron), N'-(4-bromophenyl)-N-methoxy-N-methyl urea (metobromuron), (S)-2-chloro-N-(2-ethyl-6-methyl-phenyl)-N-(2-methoxy-1-methyl-ethyl)-acetamide (metolachl or, S-metolachlor), N-(2,6-dichloro-3-methyl-phenyl)-5,7-dimethoxy-1,2,4-triazolo[1,5-a]-pyrimidine-2-sulphonamide (metosulam), N'-(3-chloro-4-methoxy-phenyl)-N,N-dimethyl-urea (metoxuron), 4-amino-6-tert-butyl-3-methylthio-1,2,4-triazin-5(4H)-one (metribuzin), N-(4-methoxy-6-methyl-1,3,5-triazin-2-yl)-N'-(2-methoxycarbonyl-phenylsulphonyl)-urea (metsulfiiron-methyl), S-ethyl-hexahydro-1H-azepine-1-carbothioate (molinate), 2-(2-naphthyloxy)-N-phenyl-propanamide (naproanilide), N-butyl-N'-(3,4-dichloro-phenyl)-N-methyl-urea (neburon), N-(4,6-dimethoxy-pyrimidin-2-yl)-N'-(3-dimethylcarbarnoyl-pyridin-2-yl-sulphonyl)-urea (nicosulfuron), S-(2-chloro-benzyl)-N,N-diethyl-thiocarbamate (orbencarb), 4-dipropylamino-3,5-dinitro-benzenesulphonamide (oryzalin), 3-[2,4-dichloro-5-(2-propinyloxy)-phenyl]-5-(t-butyl)-1,3,4-oxadiazol-2(3H)-one (oxadiargyl), 3-[2,4-dichloro-5-(1-methyl-ethoxy)-phenyl]-5-(t-butyl)-1,3,4-oxadiazol-2(3H)-one (oxadiazon), N-(4,6-dimethyl-pyrimidin-2-yl)-N'-(2-oxetan-3-yl-oxycarbonyl-phenylsulphonyl)-urea (oxasulfuron), 3-[1-(3,5-dichlorophenyl)-1-i-propyl]-2,3-dihydro-6-methyl-5-phenyl-4H-1,3-oxazin-4-one (oxaziclomefone), 2-chloro-1-(3-ethoxy-4-nitro-phenoxy)-4-trifluoromethylbenzene (oxyfluorfen), 1,1'-dimethyl-4,4'-bipyridinium (paraquat), 1-amino-N-(1-ethyl-propyl)-3,4-dimethyl-2,6-dinitro-benzene (pendimethalin), 4-(t-butyl)-N-(1-ethyl-propyl)-2,6-dinitro-benzenamine (pendralin), 4-amino-3,5,6-trichloro-pyridine-2-carboxylic acid (picloram), 2-chloro-N-(2,6-diethyl-phenyl)-N-(2-propoxy-ethyl)-acetamide (pretilachlor), N-(4-fluoro-phenyl)-6-(3-trifluoromethyl-phenoxy)-pyridine-2-carboxamide (picolinafen), N-(4,6-bisdifluoromethoxy-pyrimidin-2-yl)-N'-(2-methoxycarbonyl-phenylsulphonyl)-urea (primisulfuron-methyl), 2-chloro-N-isopropyl-N-phenyl-acetamide (propachlor), N-(3,4-dichloro-phenyl)-propanamide (propanil), 2-chloro-N-(2-ethyl-6-methyl-phenyl)-N-[(1-methyl-ethoxy)-methyl]-acetamide (propisochlor), S-phenylmethyl N,N-dipropyl-thiocarbamate (prosulfocarb), N-(4-methoxy-6-methyl-1,3,5-triazin-2-yl)-N'-(2-(3,3,3-trifluoro-propyl)-phenylsulphonyl)-urea (prosulfuron), ethyl [2-chloro-5-(4-chloro-5-difluoromethoxy-1-methyl-1H-pyrazol-3-yl)-4-fluoro-phenoxy]-acetate (pyraflufenethyl), 4-(2,4-dichloro-benzoyl)-1,3-dimethyl-5-(4-methyl-phenylsulphonyloxy)-pyrazole (pyrazolate), 4-(2,4-dichloro-benzoyl)-1,3-dimethyl-5-(phenylcarbonyl-methoxy)-pyrazole (pyrazoxyfen), N-(4,6-dimethoxy-pyrimidin-2-yl)-N'-(4-ethoxy-carbonyl-1-methyl-pyrazol-5-yl-sulphonyl)-urea (pyrazosulfuron-ethyl), O-[2,6-bis-(4,6-dimethoxy-pyrimidin-2-yl-oxy)-benzoyl]diphenylmethanone-oxime (pyribenzoxim), 6-chloro-3-phenyl4-pyridazinol (pyridafol), O-(6-chloro-3-phenyl-pyridazin-4-yl) S-octyl thiocarbonate (pyridate), 6-chloro-3-phenylpyridazin-4-ol (pyridatol), methyl 2-(4,6-dimethoxy-pyrimidin-2-yl-oxy)-benzoate (pyriminobac-methyl), 2-chloro-6-(4,6-dimethoxy-pyrimidin-2-ylthio)-benzoic acid sodium salt (pyrithiobac-sodium), 7-chloro-3-methyl-quinoline-8-carboxylic acid (quinmerac), 2-[4-(6-chloro-2-quinoxalinyloxy)-phenoxy]-propanoic acid (ethyl ester, tetrahydro-2-furanyl-methyl ester) (quizalofop, -ethyl, -P-ethyl, -P-tefuryl), N-(4,6-dimethoxy-pyrimidin-2-yl)-N'-(3-ethylsulphonyl-pyridin-2-yl-sulphonyl)-urea (rimsulfuron), 2-(1-ethoximinobutyl)-5-(2-ethylthiopropyl)-3-hydroxy-2-cyclohexen-1-one (sethoxydim), 6-chloro-2,4-bis-ethylamino-1,3,5-triazine (simazin), 2-(2-chloro-4-methyl-sulphonyl-benzoyl)-cyclohexane-1,3-dione (sulcotrione), 2-(2,4-dichloro-5-methyl-sulphonylamino-phenyl)-4-difluoromethyl-5-methyl-2,4-dihydro-3H-1,2,4-triazol-3-one (sulfentrazone), N-phosphonomethyl-glycine-trimethylsulphonium (sulfosate), N-(4,6-dimethoxy-pyrimidin-2-yl)-N'-(2-ethylsulphonyl)-imidazo[1,2-a]pyridine-3-sulphonamide (sulfosulfuron), 6-chloro-4-ethylamino-2-tert-butylamino-1,3,5-triazine (terbuthylazine), 2-tert-butylamino-4-ethylamino-6-methylthio-1,3,5-triazine (terbutryn), 2-chloro-N-(2,6-dimethyl-phenyl)-N-(3-methoxy-2-thienyl-methyl)-acetamide (thenylchlor), methyl 2-difluoromethyl-5-(4,5-dihydro-thiazol-2-yl)-4-(2-methyl-propyl)-6-trifluoromethyl-pyridine-3-carboxylate (thiazopyr), 6-(6,7-dihydro-6,6-dimethyl-3H,5H-pyrrolo[2,1-c]-1,2,4-thiadiazol-3-ylideneamino)-7-fluoro-4-(2-propinyl)-2H-1,4-benzoxazin-3(4H)-one (thidiazimin), N-(4-methoxy-6-methyl-1,3,5-triazin-2-yl)-N'-(2-methoxy-carbonyl-thien-3-yl-sulphonyl)-urea (thifensulfuron-methyl), 2-(ethoximino-propyl)-3-hydroxy-5-(2,4,6-trimethyl-phenyl)-2-cyclohexen-1-one (tralkoxydim), S-(2,3,3-trichloro-2-propenyl) diisopropylcarbamothioate (triallate), N-(4-methoxy-6-methyl-1,3,5-triazin-2-yl)-N'-[2-(2-chloro-ethoxy)-phenylsulphonyl]-urea (triasulfuron), N-methyl-N-(4-methoxy-6-methyl-1,3,5-triazin-2-yl)-N'-(2-methoxycarbonyl-phenylsulphonyl)-urea (tribenuron-methyl), (3,5,6-trichloro)-pyridin-2-yl-oxy-acetic acid (triclopyr), 2-(3,5-dichloro-phenyl)-2-(2,2,2-trichloro-ethyl)-oxirane (tridiphane), 1-amino-2,6-dinitro-N,N-dipropyl-4-trifluoromethyl-benzene (trifluralin), N-[4-dimethylamino-6-(2,2,2-trifluoro-ethoxy)-1,3,5-triazin-2-yl]-N'-(2-methoxycarbonyl-phenylsulphonyl)-urea (triflusulfuronmethyl), N-(4-methoxy-6-trifluoromethoxy-1,3,5-triazin-2-yl)-N'-(2-trifluoromethyl-phenylsulphonyl)-urea (tritosulfuron), 2-pyridinesulphonamide, N-[[(4,6-dimethoxy-2-pyrimidinyl)amino]carbonyl]-3-[methyl (methylsulphonyl)amino] (WO-A-92/10660), 2-[[[[(4,6-dimethoxy-2-pyrimidinyl)amino]carbonyl]amino]-sulphonyl]-4-[[(methylsulphonyl)amino]methyl]-methyl benzoate (DE-A 43 35 297)

("Active Compounds of Group 2")

and also, if appropriate, (c) at least one crop-plant-compatibility-improving compound from the following group of compounds:

α-(1,3-Dioxolan-2-yl-methoximino)-phenylacetonitrile (oxabetrinil), α-(cyano-methoximnino)-phenylacetonitrile (cyometrinil), 4-chloro-N-(1,3-dioxolan-2-yl-methoxy)-α-trifluoro-acetophenoneoxime (fluxofenim), 4,6-dichloro-2-phenyl-pyrimidine (fenclorim), 4-dichloroacetyl-3,4dihydro-3-methyl-2H-1,4-benzoxazine (benoxacor), 1-methyl-hexyl 5-chloro-quinoxalin-8-oxy-acetate (cloquintocet), 2,2-dichloro-N-(2-oxo-2-(2-propenylamino)-ethyl)-N-(2-propenyl)-acetamide (DKA-24), 1,8-naphthalic anhydride, ethyl 1-(2,4-dichloro-phenyl)-5-trichloromethyl-1H-1,2,4-triazole-3-carboxylate (fenchlorazol-ethyl), phenylmethyl 2-chlorotrifluoromethyl-thiazole-5-carboxylate (flurazole), 3-dichloroacetyl-5-(2-furanyl)-2,2-dimethyl-oxazolidine (furilazole, MON-13900), 4-dichloroacetyl-1-oxa-4-aza-spiro[4.5]-decane (AD-67), 2-dichloromethyl-2-methyl-1,3-dioxolane (MG-191), 2,2-dichloro-N-(1,3-dioxolan-2-yl-methyl)-N-(2-propenyl)-acetamide (PPG-1292), 2,2-dichloro-N,N-di-2-propenyl-acetamide (dichlornid), N-(4-methyl-phenyl)-N'-(1-methyl-1-phenyl-ethyl)-urea (dymron), 1-dichloroacetyl-hexahydro-3,3,8a-trimethylpyrrolo[1,2-a]-pyrimidin-6(2H)-one (BAS-145138), N-(2-methoxy-benzoyl)-4-(methylamino carbonylamino)benzenesulphonamide, ethyl 4,5-dihydro-5,5-diphenyl-3-isoxazolecarboxylate (isoxadifen-ethyl), diethyl 1-(2,4-dichlorophenyl)-4,5-dihydro-5-methyl-1H-pyrazole-3,5-dicarboxylate (mefenpyr-diethyl) and 2,4-dichlorophenoxyacetic acid (2,4-D) and its derivatives.
("Active Compounds of Group 3").

Preferred substituents of the radicals listed in the formula (I) shown above are illustrated below.

$R^1$ preferably represents in each case optionally fluorine- and/or chlorine-substituted methyl, ethyl, n- or i-propyl, n-, i-, s- or t-butyl.

$R^2$ preferably represents in each case optionally fluorine- and/or chlorine-substituted methyl, ethyl, n- or i-propyl, n-, i-, s- or t-butyl.

$R^3$ preferably represents hydrogen, fluorine, chlorine or bromine.

$R^4$ preferably represents cyano, thiocarbamoyl, fluorine, chlorine or bromine.

$R^5$ preferably represents nitro, cyano, carboxyl, carbamoyl, thiocarbamoyl, hydroxyl, mercapto, amino, hydroxyamino, aminosulphonyl, fluorine, chlorine, bromine, represents in each case optionally cyano-, hydroxyl-, methoxy-, ethoxy-, acetyl-, propionyl-, methoxycarbonyl- and/or ethoxycarbonyl-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, methylsulphonyl, ethylsulphonyl, acetyl, propionyl, n- or i-butyroyl, methoxycarbonyl, ethoxycarbonyl, n- or i-propoxycarbonyl, methylamino, ethylamino, n- or i-propylamino, n-, i-, s- or t-butylamino, represents in each case optionally cyano-, carboxyl-, fluorine-, chlorine-, bromine-, methoxycarbonyl- and/or ethoxycarbonyl-substituted ethenyl, propenyl, butenyl, ethinyl, propinyl, butinyl, propenyloxy, butenyloxy, propinyloxy or butinyloxy, represents in each case optionally fluorine- and/or chlorine-substituted acetylamino, propionylamino, methoxycarbonylamino, ethoxycarbonylarnino, methylsulphonylamino, ethylsulphonylamino, n- or i-propylsulphonylamino, n-, i-, s- or t-butylsulphonylamino, N,N-bis-methylsulphonyl-amino, N,N-bis-ethylsulphonyl-amino, N-ethylsulphonyl-N-methylsulphonyl-amino, N-acetyl-N-methylsulphonyl-amino, N-propionyl-N-methylsulphonyl-amino, N-n-butyroyl-N-methylsulphonyl-amino, N-i-butyroyl-N-methylsulphonyl-amino, N-s-butyroyl-N-methylsulphonyl-amino, N-pivaloyl-N-methylsulphonylamino, N-acetyl-N-ethylsulphonyl-amino, N-propionyl-N-ethylsulphonylamino, N-n-butyroyl-N-ethylsulphonyl-amino, N-i-butyroyl-N-ethylsulphonyl-amino, N-s-butyroyl-N-ethylsulphonyl-amino, N-pivaloyl-N-ethylsulphonyl-amino, or represents in each case optionally cyano-, fluorine-, chlorine-, bromine-, methyl-, ethyl-, n- or i-propyl-, n-, i-, s- or t-butyl-, trifluoromethyl-, metboxy-, ethoxy-, n- or i-propoxy-, difluoromethoxy- or trifluoromethoxy-substituted N-phenylcarbonyl-N-methylsulphonyl-amino, N-phenylcarbonyl-N-ethylsulphonyl-amino, N-thienylcarbonyl-N-methylsulphonyl-amino or N-thienylcarbonyl-N-ethylsulphonyl-amino.

$R^1$ particularly preferably represents in each case optionally fluorine- and/or chlorine-substituted methyl, ethyl, n- or i-propyl.

$R^2$ particularly preferably represents in each case optionally fluorine- and/or chlorine-substituted methyl, ethyl, n- or i-propyl.

$R^3$ particularly preferably represents hydrogen, fluorine or chlorine.

$R^4$ particularly represents cyano or thiocarbamoyl.

$R^5$ particularly preferably represents nitro, cyano, carboxyl, carbamoyl, thiocarbamoyl, hydroxyl, mercapto, amino, hydroxyamino, aminosuiphonyl, fluorine, chlorine, bromine, represents in each case optionally cyano-, hydroxyl-, methoxy-, ethoxy-, acetyl-, propionyl-, methoxycarbonyl- and/or ethoxycarbonyl-substituted methyl, ethyl, n- or i-propyl, methoxy, ethoxy, n- or i-propoxy, methylthio, ethylthio, n- or i-propylthio, methylsulphinyl, ethylsulphinyl, methylsulphonyl, ethylsulphonyl, acetyl, propionyl, n- or i-butyroyl, methoxycarbonyl, ethoxycarbonyl, n- or i-propoxycarbonyl, methylamino, ethylamino, n- or i-propylamino, represents in each case optionally cyano-, carboxyl-, fluorine-, chlorine-, bromine-, methoxycarbonyl- and/ or ethoxycarbonyl-substituted ethenyl, propenyl, ethinyl, propinyl, propenyloxy or propinyloxy, represents in each case optionally fluorine- and/or chlorine-substituted acetylamino, propionylamino, methoxycarbonylamino, ethoxycarbonylamino, methylsulphonylamino, ethylsulphonylamino, n- or i-propylsulphonylamino, N,N-bis-methylsulphonyl-amino, N,N-bis-ethylsulphonylamino, N-ethylsulphonyl-N-methylsulphonyl-amino, N-acetyl-N-methylsulphonyl-amino, N-propionyl-N-methylsulphonyl-amino, N-n-butyroyl-N-methylsulphonyl-amino, N-i-butyroyl-N-methylsulphonyl-amino, N-s-butyroyl-N-methylsulphonyl-amino, N-pivaloyl-N-methylsulphonyl-amino, N-acetyl-N-ethylsulphonyl-amino, N-propionyl-N-ethylsulphonyl-amino, N-n-butyroyl-N-ethylsulphonyl-amino, N-i-butyroyl-N-ethylsulphonyl-amino, N-s-butyroyl-N-ethylsulphonyl-amino, N-pivaloyl-N-ethylsulphonyl-amino, or represents in each case optionally cyano-, fluorine-, chlorine-, bromine-, methyl-, ethyl-, trifluoromethyl-, methoxy-, ethoxy-, difluoromethoxyor trifluoromethoxy-substituted N-phenylcarbonyl-N-methylsulphonyl-amino, N-phenylcarbonyl-N-ethylsulphonyl-amino, N-thienylcarbonyl-N-methylsulphonyl-amino or N-thienylcarbonyl-N-ethylsulphonyl-amino.

Examples of the compounds of the formula (I) to be used as mixing partners according to the invention which may be mentioned are:

2-(4-cyano-2-fluoro-5-methylsulphonylamino-phenyl)-4-methyl-5-trifluoromethyl-2,4-dihydro-3H-1,2,4-triazol-3-one, 2-(4-cyano-2-fluoro-5-ethylsulphonylaminophenyl)-4-methyl-5-trifluoromethyl-2,4-dihydro-3H-1,2,4-triazol-3-one, 2-(4-cyano-2-fluoro-5-methylsulphonylamino-phenyl)-4-methyl-5-difluoromethyl-2,4-dihydro-3H-1,2,4-triazol-3-one, 2-(4-cyano-2-fluoro-5-ethylsulphonylamino-phenyl)-4-methyl-5-difluoromethyl-2,4-dihydro-3H-1,2,4-triazol-3-one, 2-(4-cyano-2-fluoro-5-methylsulphonylamino-phenyl)-4-ethyl-5-trifluoromethyl-2,4-dihydro-3H-1,2,4-triazol-3-one, 2-(4-cyano-2-fluoro-5-ethylsulphonylamino-phenyl)-4-ethyl-5-trifluoromethyl-2,4-dihydro-3H-1,2,4-triazol-3-one, 2-(4-cyano-2-fluoro-5-methyl-sulphonylamino-phenyl)-4-ethyl-5-difluoromethyl-2,4-dihydro-3H-1,2,4-triazol-3-one, 2-(4-cyano-2-fluoro-5-ethylsulphonylamino-phenyl)-4-ethyl-5-difluoromethyl-2,4-dihydro-3H-1,2,4-triazol-3-one, 2-(4-thiocarbamoyl-2-fluoro-5-methylsulphonylamino-phenyl)-4-methyl-5-trifluoromethyl-2,4-dihydro-3H-1,2,4-triazol-3-one, 2-(4-thiocarbamoyl-2-fluoro-5-ethylsulphonylamino-phenyl)-4-methyl-5-trifluoromethyl-2,4-dihydro-3H-1,2,4-triazol-3-one, 2-(4-thiocarbamoyl-2-fluoro-5-methylsulphonylamino-phenyl)-4-methyl-5-difluoromethyl-2,4-dihydro-3H-1,2,4-triazol-3-one, 2-(4-thiocarbamoyl-2-fluoro-5-ethylsulphonylamino-phenyl)-4-methyl-5-difluoromethyl-2,4-dihydro-3H1,2,4-triazol-3-one, 2-(4-thiocarbamoyl-2-fluoro-5-methylsulphonylamino-phenyl)-4ethyl-5-trifluoromethyl-2,4-dihydro-3H-1,2,4-triazol-3-one, 2-(4-thiocarbamoyl-2-fluoro-5-ethylsulphonylaminophenyl)-4-ethyl-5-trifluoromethyl-2,4-dihydro-3H-1,2,4-triazol-3-one, 2-(4-thiocarbamoyl-2-fluoro-5-methylsulphonylamino-phenyl)-4-ethyl-5-difluoromethyl-2,4-dihydro-3H-1,2,4-triazol-3-one, 2-(4-thiocarbamoyl-2-fluoro-5-ethylsulphonylamino-phenyl)-4-ethyl-5-difluoromethyl-2,4-dihydro-3H-1,2,4-triazol-3-one.

The compound 2-(4-thiocarbamoyl-2-fluoro-5-ethylsulphonylamino-phenyl)-4-methyl-5-trifluoromethyl-2,4-dihydro-3H-1,2,4-triazol-3-one (I-1)—according to Chem. Abstracts also to be referred to as 4-[4,5-dihydro-4-methyl-5-oxo-(3-trifluoro-methyl)-1H-1,2,4-triazol-1-yl]-2-[(ethylsulphonyl)amino]-5-fluoro-benzenecarbothioamide (CAS Reg. No.: 173980-17-1)—may be particularly emphasised as mixing component of the formula (I).

The compounds 2-(4-cyano-2-fluoro-5-ethylsulphonylamino-phenyl)-4-methyl-5-trifluoromethyl-2,4-dihydro-3H-1,2,4-triazol-3-one (1-2)—according to Chem. Abstracts also to be referred to as N-[2-cyano-5-[4, 5-dihydro-4methyl-5-oxo-3-trifluoromethyl-1H-1,2,4-triazol-1-yl]-4fluoro-phenyl]-ethanesulphonamide (CAS Reg. No.: 157739-554)—and 2-(4-cyano-2-fluoro-5-ethylsulphonylamino-phenyl)-4-ethyl-5-trifluoromethyl-2,4-dihydro-3H-1,2,4-triazol-3-one (1-3)—according to Chem. Abstracts also to be referred to as N-[2-cyano-5-[4-ethyl4,5-dihydro-5-oxo-3-trifluoromethyl-1H-1,2,4-triazol-1-yl]-4-fluoro-phenyl]-ethanesulphonamide (CAS Reg. No.: 157739-37-2)—and 2-(4-cyano-2-fluoro-5-methylsulphonylamino-phenyl)-4-methyl-5-difluoromethyl-2,4-dihydro-3H-1,2,4-triazol-3-one (1-4)—according to Chem. Abstracts also to be referred to as N-[2-cyano-5-[3-difluoromethyl-4,5-dihydro-4-methyl-5-thioxo-1H-1,2,4-triazol-1-yl]-4-fluoro-phenyl]-methanesulphonamide (CAS Reg. No.: 15773946-3)—may furthermore be particularly emphasised as possible mixing components of the formula (I).

The compounds of the formula (I) are described in the patent applications or patents mentioned above for the N-aryl-triazolin(ethi)ones.

According to their chemical structure, the active compounds of group 2 can be assigned to the following classes of active compounds:

Amides (for example isoxaben, propanil), arylheterocycles (for example azafenidin, carfentrazone-ethyl, cinidon-ethyl, fluazolate, flumiclorac-pentyl, flumioxazin, fluthiacet-methyl, oxadiazon, oxadiargyl, pyraflufen-ethyl, pyridate, pyridafol, sulfentrazone, thidiazimin), aryloxyphenoxypropionates (for example clodinafoppropargyl, cyhalofop-butyl, diclofop-methyl, fenoxaprop-P-ethyl, fluazifop-P-butyl, haloxyfop-R-methyl, quizalofop-P-ethyl), carboxylic acid derivatives (for example clopyralid, dicamba, fluroxypyr, picloram, triclopyr), benzothiadiazoles (for example bentazone), chloroacetamides (for example acetochlor, alachlor, butachlor, dimethenamid, metazachlor, metolachlor, pretilachlor, propachlor, propisochlor), cyclohexanediones (for example butroxydim, clefoxydim, cycloxydim, sethoxydim, tralkoxydim), dinitroanilines (for example benfluralin, ethalfluralin, oryzalin, pendimethalin, trifluralin), diphenyl ethers (for example acifluorfen-sodium, aclonifen, bifenox, fluoroglycofen-ethyl, fomesafen, lactofen, oxyfluorfen), ureas (for example chlortoluron, diuron, isoproturon, linuron, metobromuron, metoxuron), imidazolinones (for example imazamethabenz-methyl, imazamox, imazaquin, imazethapyr), isoxazoles (for example isoxaflutole), nicotinanilides (for example diflufenican), nitriles (for example bromoxynil, ioxynil), organophosphorus compounds (for example glufosinate, glyphosate, sulfosate), oxyacetamides (for example flufenacet, mefenacet), phenoxycarboxylic acid derivatives (for example 2,4-D, dichlorprop, MCPA, MCPB, mecoprop), pyrazoles (for example pyrazolate, pyrazoxyfen), pyridines (for example dithiopyr, thiazopyr), pyrimidinyl(thio)benzoates (for example bispyribac, pyribenzoxim, pyrithiobac, pyriminobac), sulphonylureas (for example amidosulfuron, azimsulfuron, bensulfuron-methyl, chlorimuron-ethyl, chlorsulfuron, cinosulfuron, cyclosulfamuron, ethoxysulfuron, flupyrsulfuron-methyl-sodium, halosuilfron-methyl, imazosufiuron, metsulfuron-methyl, nicosulfuron, oxasulfuron, primisulfuron-methyl, prosulfuron, pyrazosulfuron-ethyl, rimsulfuron, sulfosulfuron, thifensulfuron-methyl, triasulfuron, tribenuron-methyl, triflusulfuron-methyl), tetrazolinones (for example fentrazamide), thiocarbamates (for example butylate, dimepiperate, EPTC, esprocarb, molinate, orbencarb, prosulfocarb, triallate), triazoles (for example amitrole), triazolopyrimidines (for example cloransulammethyl, diclosulam, florasulam, flumetsulam, metosulam), triazines (for example ametryn, atrazine, cyanazine, simazine, terbuthylazine, terbutryn), triazinones (for example hexazinone, metamitron, metribuzin), triketones (for example mesotrione, sulcotrione).

From the active compounds of group 2, the following compounds are particularly emphasised as mixing components:

Atrazine, bromoxynil, chlorimuron-ethyl, clodinafoppropargyl, dicamba, dichlorprop-P, diflufenican, dimethenamid, fenoxaprop(P)-ethyl, fentrazamide, flufenacet, flupyrsulflron-methyl-sodium, flurtamone, glufosinate-ammonium, glyphosate-isopropylammonium, imazamethapyr, imazamox, iodosulfuron-methyl-sodium, meso trione, metolachlor, metosulam, metribuzin, metsulfuron-methyl, nicosulfuron, rim-sulfuron, sulcotrione, sulfosate, sulfosulfuron, terbuthylazine, thifensulfuron-methyl, tralkoxydim, tribenuron-methyl.

According to their chemical structure, the particularly emphasised active compounds of group 2 can be assigned to the following classes of active compounds:

Aryloxyphenoxypropionates (for example clodinafop-propargyl, fenoxaprop-P-ethyl), carboxylic acid derivatives (for example dicamba, fluroxypyr), chloroacetamides (for example dimethenamid, metolachlor), cyclohexanediones (for example tralkoxydim), ureas (for example isoproturon), imidazolinones (for example imazamethabenzmethyl, imazamox), nicotineanilides (for example diflufenican), nitriles (for example bromoxynil), organophosphorus compounds (for example glufosinate, glyphosate, sulfosate), oxyacetamides (for example flufenacet), phenoxycarboxylic acid derivatives (for example dichlorpropP), sulphonylureas (for example chlorimuronethyl, flupyrsulfuron-methyl-sodium, metsulfuron-methyl, nicosulfuron, sulfosulfaron, thifensulfuron-methyl, tribenuron-methyl), triazolopyrimidines (for example florasulam, metosulam), triazines (for example ametryn, atrazine, terbuthylazine), triazinones (for example metribuzin), triketones (for example mesotrione, sulcotrione).

The compositions according to the invention preferably comprise one to three active compounds of group 2.

Surprisingly, it has now been found that the active compound combinations defined above of N-aryl-triazolin(ethi) ones of the formula (I) and the abovementioned active compounds of group 2, in addition to being very well tolerated by useful plants, have particularly high herbicidal activity and can be used in a variety of crops, in particular in barley, maize, rice and wheat, for the selective control of weeds.

Surprisingly, the herbicidal activity of the active compound combinations according to the invention of compounds of the abovementioned groups 1 and 2 is considerably higher than the sum of the effects of the individual active compounds.

This means that there is not only a complementary action but also an unforeseeable synergistic effect. The novel active compound combinations are tolerated well by a large number of crops, and the novel active compound combinations also effectively control weeds which are otherwise difficult to control. The novel active compound combinations are therefore a valuable addition to the selective herbicides.

The synergistic effect of the active compound combinations according to the invention is particularly pronounced at certain concentration ratios. However, the ratios by weight of the active compounds in the active compound combinations can be varied within relatively wide ranges. In general, from 0.01 to 1000 parts by weight, preferably from 0.02 to 500 parts by weight and particularly preferably from 0.05 to .100 parts by weight of active compound of group 2 are present per part by weight 6f the active compound of the formula (I).

Mixing components from the active compounds of group 3 which may be particularly emphasised are:

1-methylhexyl 5-chloroquinoxalin-8-oxy-acetate (cloquintocet), ethyl 1-(2,4-dichloro-phenyl)-5-trichloromethyl-1H-1,2,4-triazole-3-carboxylate (fenchlorazolethyl), ethyl 4,5-dihydro-5,5-diphenyl-3-isoxazolecarboxylate (isoxadifen-ethyl), diethyl 1-(2,4-dichlorophenyl)-4,5-dihydro-5-methyl-1H-pyrazole-3,5-dicarboxylate (mefenpyr-diethyl) and 2,4-dichlorophenoxyacetic acid (2,4-D) and its derivatives.

Surprisingly, it has been found that the active compound combinations defined above of N-aryl-triazolin(ethiones of the formula (I) or their salts and a safener/antidote ("active compounds of group 3") in combination with one or more of the active compounds of group 2 listed above, in addition to being very well tolerated by useful plants, have particularly high herbicidal activity and can be used in a variety of crops, in particular in barley, maize, rice and wheat, for the selective control of weeds.

Surprisingly, it has additionally been found that even the herbicidally active substance 2,4-dichlorophenoxy-acetic acid (2,4-D) and its derivatives can assume the safener role described above.

A particular embodiment is therefore also a mixture comprising a compound of the formula (I) and/or salts thereof on the one hand and 2,4-D and/or its derivatives on the other hand, if appropriate in combination with one or more of the abovementioned active compounds of group 2. Typical derivatives of 2,4-D are, for example, its esters.

The compounds diethyl 1-(2,4-dichlorophenyl)-4,5-dihydro-5-methyl-1H-pyrazole-3,5-dicarboxylate (mefenpyr-diethyl), 1-methylhexyl [(5-chloro-8-quinolinyl)oxy]acetate (cloquintocet-mexyl) and ethyl 1-(2,4-dichlorophenyl)-5-(trichloromethyl)-1H-1,2,4-triazole-3-carboxylate (fenchlorazole-ethyl) are described in the following patent applications: DE-A-39 39 503, EP-A-191 736 and DE-A-35 25 205, respectively. 2,4-D is a known herbicide.

Here it is surprising that, from a large number of known safeners or antidotes capable of antagonising the damaging effect of a herbicide on the crop plants, it is specifically the active compounds of group 3 listed above which neutralise the damaging effect of compounds of the formula (I) and their salts, if appropriate in combination with one or more of the active compounds of group 2 listed above, on the crop plants virtually completely without adversely affecting the herbicidal activity against the weeds.

The particularly advantageous effect of the particularly preferred combination partners of group 3, in particular with respect to sparing cereal plants, such as, for example, wheat, barley and rye, may be emphasised here.

The advantageous effect of the crop plant compatibility of the active compound combinations according to the invention is likewise particularly strongly pronounced at certain concentration ratios. However, the ratios by weight of the active compounds in the active compound combinations can be varied within relatively wide ranges. In general, from 0.001 to 1000 parts by weight, preferably from 0.01 to 100 parts by weight and particularly preferably from 0.1 to 10 parts by weight of one of the compounds, mentioned above under (c), which improve compatibility with crop plants (antidotes/safeners) are present per part by weight of active compound of the formula (I), its salts or its mixtures with active compounds of group 2.

According to the invention, it is possible to treat all plants and parts of plants. By plants are understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant vareties which can or cannot be protected by varietal property rights. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, fuirthermore by one- or multi-layer coating.

Among the plants obtained by biotechnological or genetic engineering methods or by combinations of these methods, emphasis is given to those plants which tolerate the so-called 4HPPD, EPSP and/or PPO inhibitors, such as, for example, Acuron plants.

The active compound combinations according to the invention can be used, for example, in connection with the following plants:

Dicotyledonous weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindemia, Lamium, Veronica, Abutilon, Emex, Datura, Viola, Galeopsis, Papaver, Centaurea, Trifolium, Ranunculus* and *Taraxacum*.

Dicotyledonous crops of the genera: *Gossypium, Glycine, Beta, Daucus, Phaseolus, Pisum, Solanum, Linum, Ipornoea, Vicia, Nicotiana, Lycopersicon, Arachis, Brassica, Lactuca, Cucumis* and *Cucurbita*.

Monocdtyledonous weeds of the genera: *Echinochloa, Setaria, Panicum, Digitaria, Phleum, Poa, Festuca, Eleusine, Brachiaria, Loliumn, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera* and *Phalaris*.

Monocotyledonous crops of the genera: *Oryza, Zea, Triticum, Hordeum, Avena, Secale, Sorghum, Panicum, Saccharum, Ananas, Asparagus* and *Allium*.

However, the use of the active compound combinations according to the invention is in no way restricted to these genera, but also extends in the same manner to other plants.

The active compound combinations can be converted into the customary formulations, such as solutions, emulsions, wettable powders, suspensions, powders, dusts, pastes, soluble powders, granules, suspo-emulsion concentrates, natural and synthetic substances impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

If the extender used is water it is also possible to use, for example, organic solvents as auxiliary solvents. Suitable liquid solvents are in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

Suitable solid carriers are:

for example ammonium salts and ground natural minerals, such as kaolins, clays, talc, chalk, quartz, attapulgite, montrnorillonite or diatomaceous earth, and ground synthetic minerals, such as finely divided silica, alumina and silicates; suitable solid carriers for granules are: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; suitable emulsifying and/or foam-forming agents are: for example nonionic and anionic emulsifiers, such as polyoxyethylene fatty acid esters, polyoxyethylene fatty alcohol ethers, for example alkylaryl polyglycol ethers, alkylsulphonates, alkylsulphates, arylsulphonates as well as protein hydrolysates; suitable dispersing agents are: for example lignin-sulphite waste liquors and methylcellulose.

Tackifiers such as carboxyrnethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general comprise between 0.1 and 95 per cent by weight, preferably between 0.5 and 90%, of active compounds.

In general, the active compound combinations according to the invention are applied in the form of ready mixes. However, the active compounds which the active compound combinations comprise can also be formulated individually and mixed upon use, i.e. applied in the form of tank mixes.

The novel active compound combinations can be used as such or in the form of their formulations, and furthermore also as mixtures with other known herbicides, ready mixes or tank mixes again being possible. They may also be mixed with other known active compounds, such as fingicides, insecticides, acaricides, nematicides, bird repellents, growth substances, plant nutrients and agents which improve soil structure. For particular application purposes, in particular when applied post-emergence, it may furthermore be advantageous to incorporate, in the formulations, mineral or vegetable oils which are tolerated by plants (for example the commercial product "Oleo DuPont 11E") or ammonium salts such as, for example, ammonium sulphate or ammonium thiocyanate, as further additives.

The novel active compound combinations can be used as such, in the form of their formulations or in the use forms prepared therefrom by further dilution, such as ready-to-use solutions, suspensions, emulsions, powders, pastes and granules. They are used in the customary manner, for example by watering, spraying, atomising, dusting or scattering.

The active compound combinations according to the invention can be applied before and after the plants have emerged, that is to say pre-emergence and post-emergence. They can also be incorporated into the soil before sowing.

The good herbicidal activity of the novel active compound combinations can be seen from the examples which follow. While the individual active compounds show weak points regarding the herbicidal activity, the combinations, without exception, display a very good activity against weeds, which exceeds a simple additive effect.

A synergistic effect in herbicides is always present when the herbicidal activity of the active compound combination exceeds the activity of the active compounds when applied individually.

The expected activity for a given combination of two herbicides can be calculated as follows (cf. COLBY, S. R.: "Calculating synergistic and antagonistic responses of herbicide combinations", Weeds 15, pages 20-22, 1967):

| If | |
|---|---|
| X = | % damage by herbicide A (active compound of the formula I) at an application rate of p kg/ha |
| and | |
| Y = | % damage by herbicide B (active compound of the formula II) at an application rate of q kg/ha |
| and | |
| E = | the expected damage of the herbicides A and B at application rates of p and q kg/ha, |
| then | |
| E = | X + Y − (X * Y/100). |

If the actual damage exceeds the calculated value, then the activity of the combination is superadditive, i.e. a synergistic effect exists.

What is claimed is:

1. A novel herbicidal composition comprising:
an effective amount of a synergistic combination of two or more active compounds, wherein said combination of said active compounds includes the combination of 2-(4-thiocarbamoyl-2-fluoro-5-ethylsulphonylaminophenyl)-4-methyl-5-trifluoromethyl-2,4-dihydro-3H-1,2,4-triazol-3-one as a first active compound, with a member selected from the group consisting of sulfonylureas and triazolopyrimidines as a second active compound, and optionally, one or more crop-plant-compatibility improving compounds selected from the group consisting of α-(1,3-Dioxolan-2-yl-methoximino)-phenylacetonitrile (oxabetrinil), α-(cyanomethoximino)-phenylacetonitrile (cyometrinil), 4-chloro-N-(1,3-dioxolan-2-yl-methoxy)-α-trifluoro-acetophenoneoxime (fluxofenim), 4,6-dichloro-2-phenyl-pyrimidine (fenclorim), 4-dichloroacetyl-3,4-dihydro-3-methyl-2H-1,4-benzoxazine (benoxacor), 1-methyl-hexyl 5-chloroquinoxalin-8-oxy-acetate (cloquintocet), 2,2-dichloro-N-(2-oxo-2-(2-propenyl-amino)-ethyl)-N-(2-propenyl)-acetamide (DKA-24), 1,8-naphthalic anhydride, ethyl 1-(2,4-dichloro-phenyl)-5-trichloromethyl-1H-1,2,4-triazole-3-carboxylate (fenchlorazol-ethyl), phenylmethyl 2-chloro-4-trifluoromethyl-thiazole-5-carboxylate (flurazole), 3-dichloroacetyl-5-(2-furanyl)-2,2-dimethyl-oxazolidine (furilazole, MON-13900), 4-dichloroacetyl-1-oxa-4-aza-spiro[4.5]-decane (AD-67), 2-dichloromethyl-2-methyl-1,3-dioxolane (MG-191), 2,2-dichloro-N-(1,3-dioxolan-2-yl-methyl)-N-(2-propenyl)-acetamide (PPG-1292), 2,2-dichloro-N,N-di-2-propenyl-acetamide (dichlormid), N-(4-methyl-phenyl)-N'-(1-methyl-1-phenyl-ethyl)-urea (dymron), 1-dichloroacetyl-hexahydro-3,3,8a-trimethyl-pyrrolo[1,2-a]-pyrimidin-6(2H)-one (BAS-145138), N-(2-methoxy-benzoyl)-4-(methylaminocarbonylamino)-benzenesulphonamide, ethyl 4,5dihydro-5,5-diphenyl-3-isoxazolecarboxylate (isoxadifen-ethyl), diethyl 1-(2,4-dichloropheny)-4,5-dihydro-5-methyl-1H-pyrazole-3,5-dicarboxylate (mefenpyr-diethyl) and 2,4-dichlorophenoxyacetic acid (2,4-D) and its derivatives.

2. The herbicidal composition of claim 1, wherein said sulfonylurea is selected from the group consisting of amidosulfuron, azimsulfuron, bensulfuron-methyl, chlorimuron-ethyl, chlorsulfuron, cinosulfuron, cyclosulfamuron, ethoxysulfuron, flupyrsulfuron-methyl-sodium, halosulfuron-methyl, imazosulfuron, metsulfuron-methyl, nicosulfuron, oxasulfuron, primisulfuron-methyl, prosulfuron, pyrazosulfuron-ethyl, rimsulfuron, sulfosulfuron, thifensulfuron-methyl, triasulfuron, tribenuron-methyl, triflusulfuron-methyl and iodosulfuron-methyl-sodium.

3. The herbicidal composition of claim 1 wherein said triazolopyrimidine is selected from the group consisting of cloransulam-methyl, diclosulam, florasulam, flumetsulam, metosulam.

4. The herbicidal composition according to claim 1, wherein said crop-plant-compatibility improving compound is selected from the group consisting of 1-methylhexyl 5-chloro-quinoxalin-8-oxy-acetate (cloquintocet), ethyl 1-(2,4-dichloro-phenyl)-5trichloromethyl-1H-1,2,4-triazole-3-carboxylate (fenchlorazol-ethyl), ethyl-4,5-dihydro-5, 5-diphenyl-3-isoxazolecarboxylate (isoxadifen-ethyl), diethyl 1-(2,4-dichlorophenyl)-4,5-dihydro-5-methyl-1H-pyrazole-3,5-dicarboxylate (mefenpyr-diethyl) and 2,4-dichlorophenoxyacetic acid (2,4-D) and its derivatives.

5. The herbicidal composition according to any one of claims 1 through 4, wherein from 0.01 to 1000 parts by weight, preferably from 0.02 to 500 parts by weight, particularly preferably from 0.05 to 100 parts by weight of said second active compound is present per part by weight of said first active compound.

6. A method for controlling undesirable plants comprising the step of applying an effective amount of the herbicidal composition according to any one of claims 1 through 4 to a member selected from the group consisting of said plant, a habitat of said plant, and combinations thereof.

7. A method for controlling undesirable plants comprising the step of applying an effective amount of the herbicidal composition according to claim 5 to a member selected from the group consisting of said plant, a habitat of said plant, and combinations thereof.

* * * * *